United States Patent [19]
Mahony

[11] 4,356,731
[45] Nov. 2, 1982

[54] METHOD AND MEANS FOR GENERATING TIME GAIN COMPENSATION CONTROL SIGNAL FOR USE IN ULTRASONIC SCANNER AND THE LIKE

[75] Inventor: John E. Mahony, Sacramento, Calif.

[73] Assignee: General Electric Company, Ranco Cordova, Calif.

[21] Appl. No.: 203,661

[22] Filed: Nov. 3, 1980

[51] Int. Cl.³ .............................................. G01N 29/04
[52] U.S. Cl. ......................................... 73/631; 73/900
[58] Field of Search ................................... 73/631, 900

[56] References Cited
U.S. PATENT DOCUMENTS

| | | | |
|---|---|---|---|
| 3,033,029 | 5/1962 | Weighart | 73/631 |
| 3,367,173 | 2/1968 | Uphoff | 73/631 |
| 4,102,205 | 7/1978 | Pies et al. | 73/631 |

*Primary Examiner*—James J. Gill
*Attorney, Agent, or Firm*—Flehr, Hohbach, Test, Albritton & Herbert

[57] ABSTRACT

Time gain compensation is provided in an ultrasonic scanner by storing a digital code in memory representing the desired signal gain for intervals of time during the reflected wave. Gain compensation due to transducer parameter can be provided in digital form in a separate memory, and the outputs of the two memories are combined and applied to a digital to analog converter. The resulting analog control signal is preferably filtered and then applied as a control signal to a gain control amplifier.

11 Claims, 10 Drawing Figures

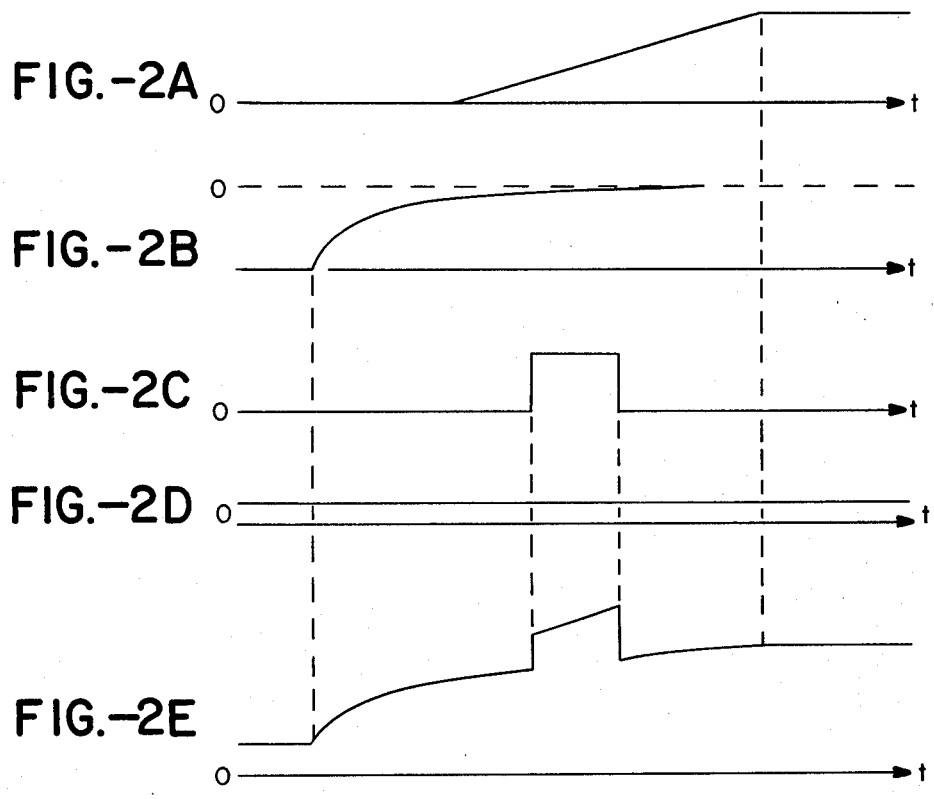
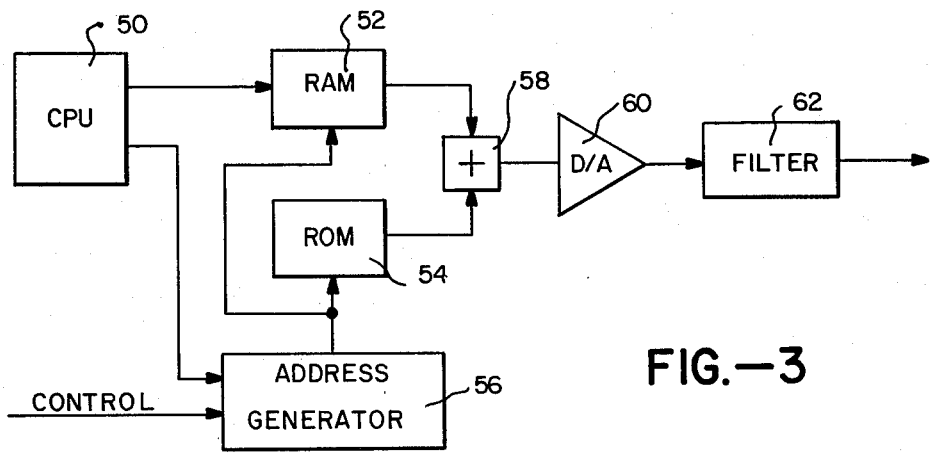

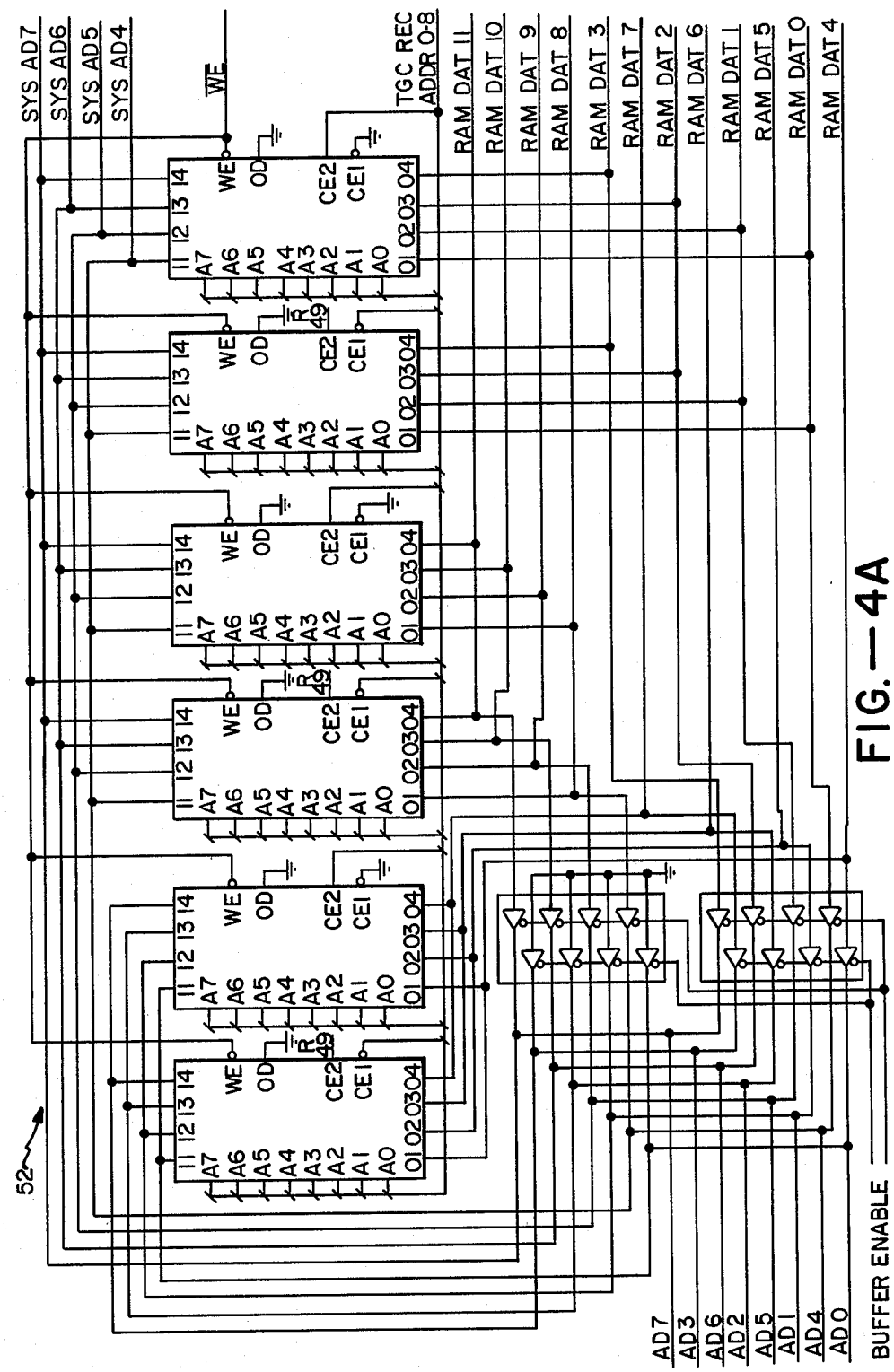
FIG.—4A

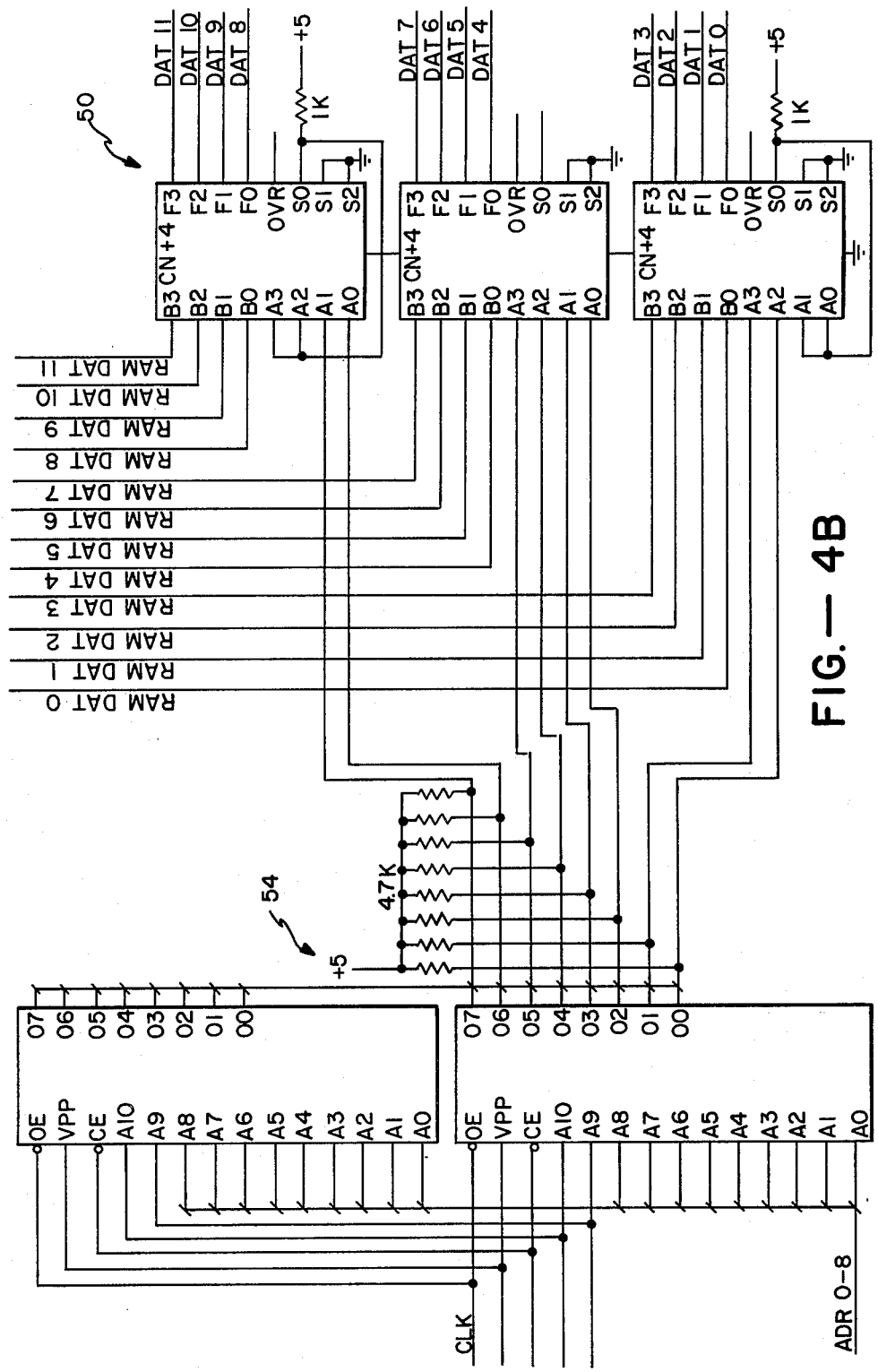
FIG.—4B

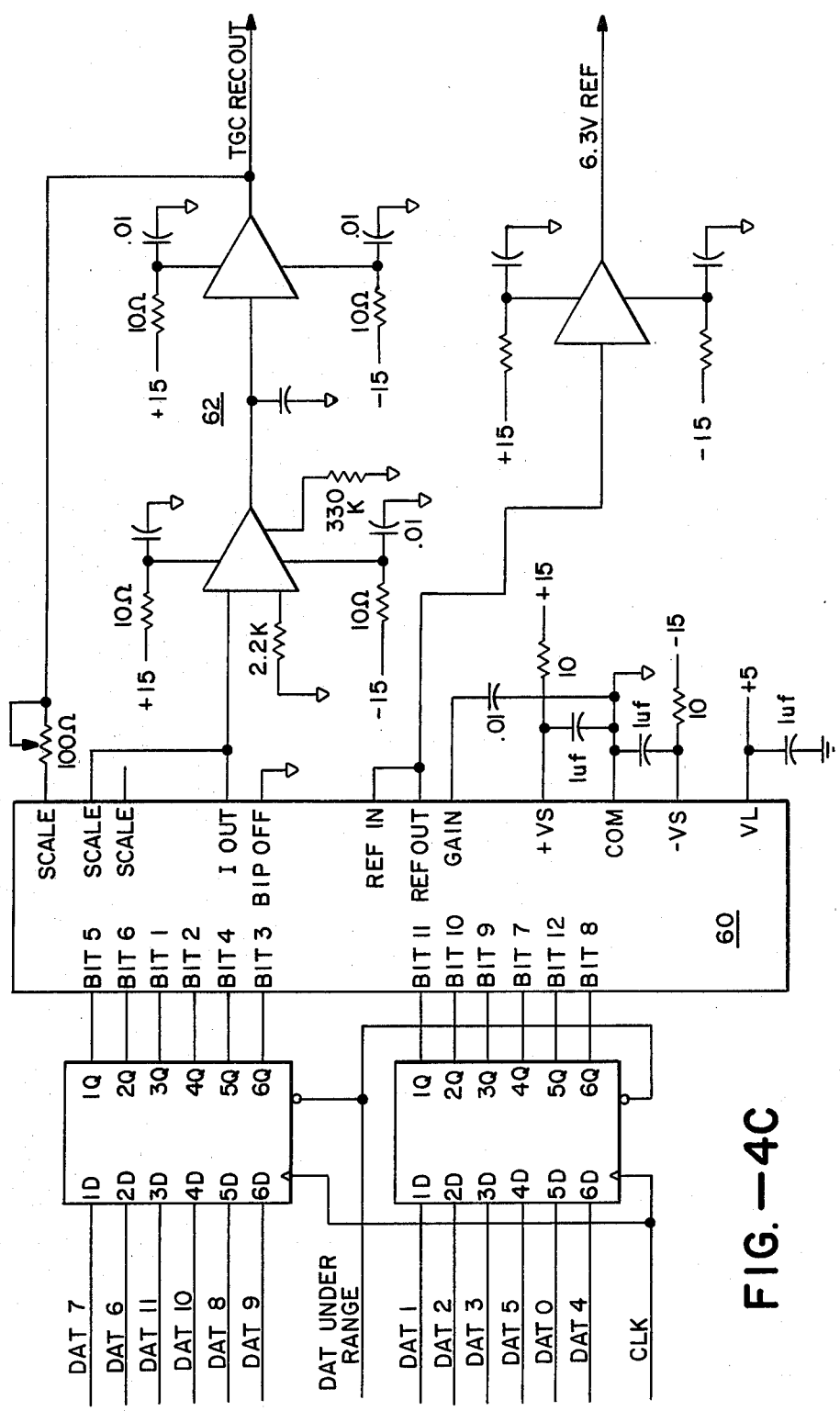
FIG.—4C

METHOD AND MEANS FOR GENERATING TIME GAIN COMPENSATION CONTROL SIGNAL FOR USE IN ULTRASONIC SCANNER AND THE LIKE

This invention relates generally to ultrasonic scanners such as used for medical diagnostic purposes, and more particularly the invention relates to a method and means for compensating reflected ultrasonic signals to enhance analysis thereof.

Ultrasonic diagnostic systems are known and commercially available for diagnostic purposes. See for example U.S. Pat. No. 4,172,386 for "Video A Trace Display System For Ultrasonic Diagnostic System" and U.S. Pat. No. 4,204,433 for "Computerized Ultrasonic Scanner With Technique Select." The commercially available Datason ultrasound system of General Electric Company provides both real time and static images on a television display.

Briefly, such systems utilize sound transducers to transmit ultrasonic (e.g. on the order of several megahertz) waves into a patient and to receive echo signals. In one mode of operation, the transducer is attached to a plurality of hinged arms for movement in a single plane, and potentiometers associated with the hinged arms produce signals which identify the transducer position. Alternatively, a transducer array or a hand held transducer can be used. The echo signals are applied to a time gain compensated amplifier to adjust the echo signals for attenuation in passing through the patient. The adjusted signals are then passed through an analog to digital conversion and video processing circuitry and thence to scan converter circuitry for display formatting. The display comprises a plurality of pixels in horizontal rows and vertical columns with each pixel having a brightness level in response to the input signal. Conventionally, the brightness is defined by a 32 level Gray-scale, hence the pixel brightness level requires a five bit digital code.

Heretofore, the control signal for the time gain compensated amplifier has been generated by combining analog signal components to effect the desired amplifier response. However, accuracy of control is limited in said systems, and the code parameters cannot be revised easily once defined in hardware. Moreover, transducers have different response characteristics which must be accounted for in the time gain compensated amplifier. Accordingly, resolution is limited in using the analog signals.

An object of the present invention is a method of improving the time gain compensation of reflected signals in an ultrasonic scanner.

Another object of the invention is means for generating a time gain compensation control signal in which signal parameters can be readily changed.

Still another object of the invention is an ultrasonic scanner with improved display resolution.

Briefly, in accordance with the invention a time gain compensation signal for use in an ultrasonic scanner and the like is generated by storing in a first memory a digital code indicative of desired amplifier gain. An electrical signal is generated in response to reflections of an ultrasonic wave, and the generated electrical signal is applied to a variable gain amplifier means. The stored digital code is applied to a digital to analog converter means, and the analog signal derived therefrom is applied as a control signal to the variable gain amplifier. The digital code and the analog code signal are time correlated to the ultrasonic wave whereby the gain of the variable gain amplifier is adjusted for each unit length of ultrasonic wave reflection path.

In a preferred embodiment a second digital code is stored in a second memory with the second digital code being indicative of transducer response characteristics. The analog conversion means includes arithmetic means for combining the first digital code indicative of gain and the second digital code indicative of transducer response characteristics prior to driving the digital to analog converter. Advantageously, the output of the digital to analog converter is applied through a low pass filter having a limited output slew rate and thereby smooths the analog amplifier control signal.

The first memory means is preferably a random access memory which can be loaded and altered by suitable computer means to achieve a desired amplifier response. The second memory means is preferably a read only memory which is programmed in accordance with a particular transducer characteristic.

The invention and objects and features thereof will be more readily apparent from the following detailed description and appended claims when taken with the drawings, in which:

FIGS. 2A–2E are waveforms illustrating the conventional analog method of deriving a time gain compensation control signal.

FIG. 3 is a functional block diagram of one embodiment of time gain compensation control signal means in accordance with the present invention.

FIGS. 4A–4C are detailed functional block diagrams of the circuit of FIG. 3.

Figure 1:
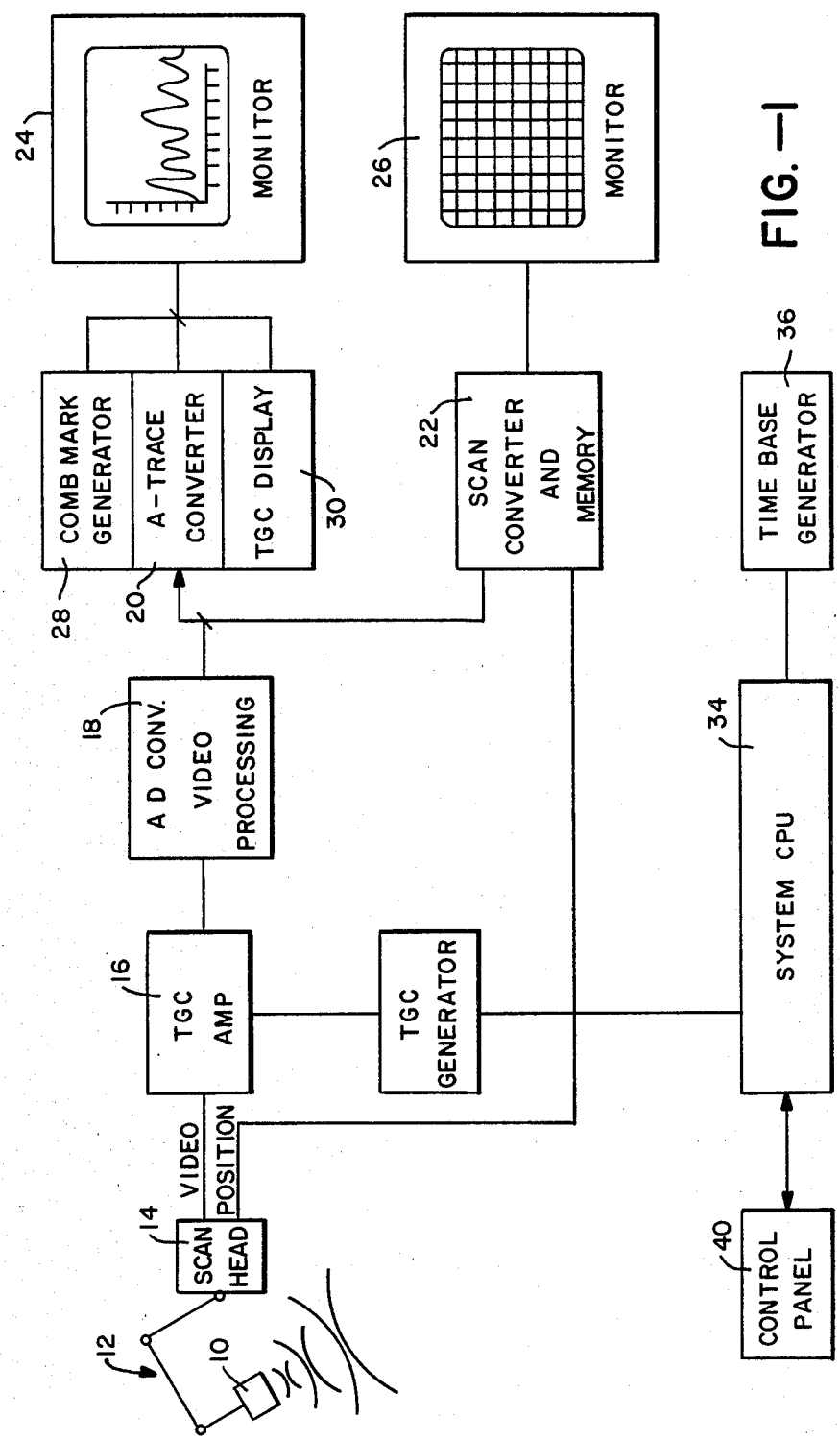
FIG. 1 is a functional block diagram of an ultrasonic scanner system.

Referring now to the drawings, FIG. 1 is a functional block diagram of an ultrasonic scanner. The system includes a transducer 10 mounted on a hinged arm system shown generally at 12 whereby transducer 10 can move freely in a single plane. Potentiometers in scan head 14 and associated with the arms of the system generate signals indicative of the X and Y position of the scanner 10 in the plane of motion.

Transducer 10 transmits ultrasonic signals (e.g. on the order of 2 megahertz) and generates electrical signals in response to reflections of the transmitted ultrasonic signals. The generated signals are attenuated in time due to attenuation of the ultrasonic signal in passing through a patient.

The attenuated video signal is then applied to a time gain compensated amplifier 16, and the amplified signal is then applied to analog to digital conversion and video processing circuitry 18. The output of circuitry 18 is then applied to A trace converter circuitry 20 and to scan converter and memory circuitry 22 which generate the signals for controlling television monitors 24 and 26, respectively.

The A trace converter generates a signal for real time display of the amplitude of each reflected ultrasonic wave. The A trace data applied to monitor 24 identifies a horizontal position on the monitor (e.g. 1,000 positions) and an amplitude or vertical position associated with each X position. This data controls the intensity of the electron beam in the display during raster scanning of the beam. Scale markings for the displayed A trace are generated by comb mark generator 28, and a time gain compensation curve is provided by generator 30.

A section view of the patient is displayed on monitor 26 in response to the scan converter and memory 22.

The signal from circuitry 18 is converted for storage in a 512×512 memory matrix with each point in the matrix accommodating a 5 bit brightness code. The matrix corresponds to the pixels on the display of monitor 26 with the brightness code being indicative of the Grayscale for the pixels.

System control is provided by a central processing unit 34 which also controls a time base generator 36 which generates the timing signals for the system. A time gain compensation (TGC) control generator 38 generates the control signal for amplifier 16 and a control panel 40 is provided for manual control of the system through the central processing unit.

Heretofore, the TGC generator 38 has comprised hard wired circuitry for generating the amplifier control signal by combining a plurality of analog signals, such as illustrated in FIGS. 2A–2E. For example, in FIG. 2A a ramp voltage component provides a linear increase in control voltage with respect to time in order to compensate for signal attenuation as the ultrasonic wave travels through a patient. In FIG. 2B a faster rising signal component of the control signal is provided to account for the rapid increase in attenuation in the initial time period of the reflected wave. If more detailed analysis is desired of an object within the patient, the control signal can be increased during a window or time period when a reflected wave is received from this object, as noted by the square wave component in FIG. 2C. Finally, an initial offset in gain is established by the signal component in FIG. 2D. FIG. 2E is a composite wave formed by summing the components of FIGS. 2A–2E.

Since the circuitry for generating the control signal component, illustrated in FIGS. 2A–2D, is hard wired, the ability to modify the composite wave is severely limited. The difficulty in adjusting the TGC control signal is compounded since transducers have different response characteristics.

In accordance with the present invention a gain value is established for each point of a reflected ultrasonic wave and the gain value in digital form is stored in a random access memory. The memory is repetitively read and applied to digital to analog converter means for generating the control signal for the TGC amplifier. By using a digital code in memory, modifications to the code are readily implemented through the system processor. Further, a second memory means can be provided to adjust the digital code in accordance with parameters of a particular transducer.

FIG. 3 is a functional block diagram of one embodiment of apparatus in accordance with the invention. The system CPU 50 generates and stores the gain value for each point of reflected wave in random access memory 52. A digital code representative of the characteristics of a particular transducer is stored in a programmable read only memory 54. In generating the TGC control signal, memory 52 and memory 54 are sequentially addressed by generator 56 and the two digital outputs are combined in adder 58. The combined digital signal is then applied to digital to analog converter 60 which generates the corresponding analog voltage. This analog voltage is then applied to a low pass filter 62 which limits the output slew rate whereby spurious signals or glitches are eliminated while allowing the analog signal to pass smoothly.

FIGS. 4A–4C are detailed functional block diagrams of the circuit of FIG. 3 as implemented in the Datason ultrascan system. The same reference numerals are used for the elements. The Datason system utilizes an Intel 8085 microprocessor, and the random access memory 52 comprises six (AMD 91LO1C) 256 by 4 bit rams to provide 512 addresses each having 12 bits of storage. The prom 54 comprises two (Intel 2716) proms to provide 4096 addresses each storing eight bits. The memories are addressed at a clock rate to allow each address to control the gain for 1 millimeter of display. The prom output is subtracted from the RAM output in the serially connected AMD 25LS 2517 ALU subtractors 50. The digital output is then applied to a Burr-Brown DAC 80-12 bit converter 60, and the analog signal is then passed through a filter 62 comprising an RCA CA 3080A amplifier and a serial connected National LM 310 amplifier.

By storing digital data in memory representing the values of amplifier gain modifications of the data is readily implemented by changing the stored data words. Adapting a desired control signal to a particular transducer is readily implemented by substituting proms in the system.

While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. A method of generating a time gain compensated signal in an ultrasonic scanner and the like comprising the steps of generating electrical signals in response to reflections of an ultrasonic wave, applying said electrical signals to a variable gain amplifier, storing digital codes indicative of desired gains in a random access memory, selectively addressing said random access memory whereby a variable digital code is obtained, applying said digital code to a digital to analog converter means to thereby derive an analog control signal, and applying said analog control signal to control the gain of said variable gain amplifier.

2. The method as defined by claim 1 wherein said analog control signal is correlated to an ultrasonic wave whereby gain is adjusted for each unit length of ultrasonic wave reflection path.

3. The method as defined by claim 2 wherein said unit of reflection path is one millimeter.

4. The method as defined by claim 1 and further including the step of storing a digital code indicative of transducer response characteristics, combining said second digital code with said first digital code, applying said combined digital codes to said analog converter means.

5. The method as defined by claim 4 and further including the step of filtering said analog control signal by low pass filter means.

6. The method as defined by claim 1 and further including the step of storing a second digital code indicative of transducer response characteristics, applying said second digital code to digital to analog converter means to thereby derive a second analog signal, and combining said analog control signal and said second analog signal.

7. In an ultrasonic scanner having a variable gain amplifier for amplifying a time attenuated signal, means for generating a control signal for said variable gain amplifier comprising a first random access digital memory means, means for loading first digital codes indicative of gain in said first random access memory means, digital to analog conversion means, means for selectively addressing said first random access memory whereby a variable digital code is obtained, means for applying said first digital code to said digital to analog converter means and thereby generating an analog signal, and means for applying said analog signal to the variable gain amplifier in time correlation with said time attenuated signal.

8. Means as defined by claim 7 wherein said first digital code includes a plurality of digital words with each digital word indicative of gain at a time interval.

9. Means for generating a control signal as defined by claim 8 and further including a second memory means for storing a second digital code indicative of transducer response characteristics, said digital to analog conversion means including means for arithmetically combining said first digital code and said second digital code prior to generating said analog signal.

10. Means for generating a control signal as defined by claim 7 or 8 and further including low pass filter means and means interconnecting said low pass filter means with said digital to analog conversion means for filtering said analog signal.

11. Means for generating a control signal as defined by claim 10 wherein said second memory means comprises a read only memory.

* * * * *